(12) United States Patent
Tan

(10) Patent No.: US 11,638,830 B2
(45) Date of Patent: May 2, 2023

(54) VOLTAGE CONVERTER FOR MEDICAL DEVICES

(71) Applicant: Min Tan, Shenzhen (CN)

(72) Inventor: Min Tan, Shenzhen (CN)

(73) Assignee: Dongguan Bang Bang Tang Electronic Technologies Co., Ltd., Guangdong (CN)

( * ) Notice: Subject to any disclaimer, the term of this patent is extended or adjusted under 35 U.S.C. 154(b) by 372 days.

(21) Appl. No.: 17/089,706

(22) Filed: Nov. 4, 2020

(65) Prior Publication Data

US 2021/0052905 A1    Feb. 25, 2021

Related U.S. Application Data

(60) Continuation-in-part of application No. 15/970,898, filed on May 4, 2018, now Pat. No. 10,870,010, which is a division of application No. 15/372,410, filed on Dec. 8, 2016, now Pat. No. 10,016,611.

(51) Int. Cl.
  *A61N 1/36*     (2006.01)
  *A61N 1/378*    (2006.01)
  *H03G 3/30*     (2006.01)
  *H03G 3/00*     (2006.01)

(52) U.S. Cl.
  CPC ........... *A61N 1/3787* (2013.01); *A61N 1/378* (2013.01); *H03G 3/002* (2013.01); *H03G 3/30* (2013.01)

(58) Field of Classification Search
  CPC .............................. A61N 1/378; A61N 1/3787
  See application file for complete search history.

(56) References Cited

U.S. PATENT DOCUMENTS

| 5,522,865 | A | * | 6/1996 | Schulman | A61N 1/37252 607/57 |
| 5,876,425 | A | * | 3/1999 | Gord | A61N 1/36038 607/57 |
| 2016/0029998 | A1 | * | 2/2016 | Brister | A61B 8/0833 600/424 |

* cited by examiner

*Primary Examiner* — Michael J D'Abreu

(57) ABSTRACT

A voltage converter for medical devices includes a switch capacitor converter core including a plurality of power transistor switches configured to receive an input voltage and output an output voltage; a switch driver connected with the switch capacitor converter core and configured to turn on corresponding power transistor switches in the switch capacitor converter core so as to supply power to a load receiving the output voltage; a switch signal router connected with the switch driver and configured to selectively transmit signals required by the switch driver; a gain selection decoder connected with the switch signal router; a gain controller connected with the gain selection decoder, the gain selection decoder being configured to decode gain selection instructions transmitted from the gain controller; an input adjusting device connected with the gain controller and configured to receive the input voltage and a reference voltage, to indicate relationship between the input voltage and the reference voltage, and to transmit the relationship to the gain controller; and an output adjusting device connected with the gain controller and configured to receive the output voltage and the reference voltage, to indicate relationship between the output voltage and the reference voltage, and to transmit the relationship to the gain controller.

9 Claims, 3 Drawing Sheets

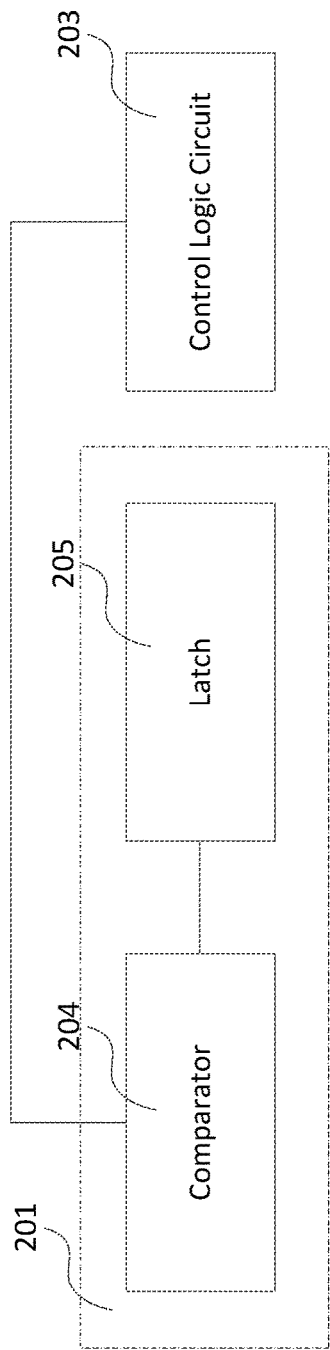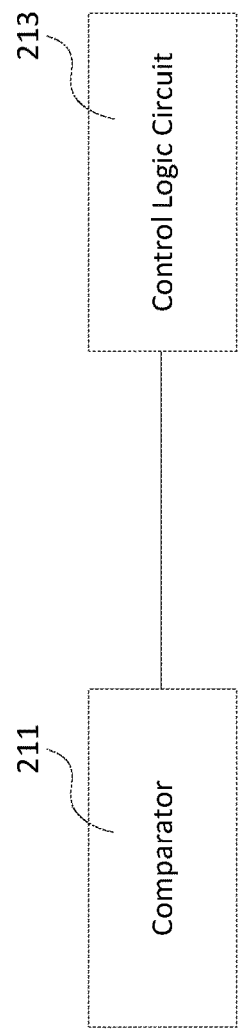
FIG. 2A
FIG. 2B

VOLTAGE CONVERTER FOR MEDICAL DEVICES

CROSS-REFERENCE TO RELATED APPLICATIONS

This application claims the benefit of U.S. non-provisional patent application Ser. No. 15/970,898 filed on May 4, 2018, which is a divisional application of U.S. non-provisional patent application Ser. No. 15/372,410 filed on Dec. 8, 2016, now U.S. Pat. No. 10,016,611; the contents of which is hereby incorporated by reference.

FIELD OF THE PATENT APPLICATION

The present patent application generally relates to medical electronics and more specifically to a voltage converter for medical devices.

BACKGROUND

Implantable medical devices have been applied more and more widely in modern medicine. Because of its unique applications, an implantable medical device generally requires the power supply that supplies power to it to be small volume, low power and high power transfer efficiency. Not only so, the implantable medical device but also generally has multiple working modes, such as a sleep mode, a measurement mode, a data transmission mode, and so on. In each different working mode, the same implantable medical device typically has a different requirement on the power supply that supplies power to it.

Voltage converter is an important component of a power supply system of an implantable medical device. Conventional voltage converters usually cannot effectively satisfy different requirements of the implantable medical device in different working modes on the output voltage and the load values, which are in a relatively wide range. In addition, to improve the configurability, conventional voltage converters usually have relatively complicated circuits, relatively large chip areas, relatively high power consumption, and relatively low system working efficiency, and therefore are not suitable for supplying power to medical devices.

SUMMARY

The present patent application is directed to a voltage converter for medical devices. In one aspect, the voltage converter includes: a switch capacitor converter core including a plurality of power transistor switches configured to receive an input voltage and output an output voltage; a switch driver connected with the switch capacitor converter core and configured to turn on corresponding power transistor switches in the switch capacitor converter core so as to supply power to a load receiving the output voltage; a switch signal router connected with the switch driver and configured to selectively transmit signals required by the switch driver; a gain selection decoder connected with the switch signal router; a gain controller connected with the gain selection decoder, the gain selection decoder being configured to decode gain selection instructions transmitted from the gain controller; an input adjusting device connected with the gain controller and configured to receive the input voltage and a reference voltage, to indicate relationship between the input voltage and the reference voltage, and to transmit the relationship to the gain controller; an output adjusting device connected with the gain controller and configured to receive the output voltage and the reference voltage, to indicate relationship between the output voltage and the reference voltage, and to transmit the relationship to the gain controller; a clock generator connected with the switch signal router, the gain controller and the output adjusting device; and a counter connected with the gain controller. The input adjusting device includes an adaptive ADC configured to determine a required conversion gain ratio based on the input voltage and the reference voltage, and a control logic circuit connected with the adaptive ADC and configured to control the adaptive ADC. The output adjusting device includes a plurality of comparators and a control logic circuit connected with the comparators. The gain controller is configured to control the conversion gain ratio required by the switch capacitor converter core according to information provided by the input adjusting device and the output adjusting device, the conversion gain ratio being the ratio between the output voltage and the input voltage. When the output voltage is in a threshold range below the reference voltage, the gain controller is turned off, and switching frequency of the switch capacitor converter core is adjusted by discrete amounts based on a DFS (Discrete-frequency Scaling) algorithm so that the output voltage gradually approaches the reference voltage. When the output voltage is equal to or greater than the reference voltage, the switch capacitor converter core stops its switching operations. When the output voltage is lower than the reference voltage, the switch capacitor converter core is configured to resume its switching operations.

The switch capacitor converter core may include a plurality of power transistor switches and a pump capacitor, and the conversion gain ratio provided by the switch capacitor converter core may be 1/2, 2/3, 1, 3/2 or 2.

The adaptive ADC in the input adjusting device may include a comparator and a plurality of latches, the latches being connected with the comparator and configured to generate data of a predetermined number of digits according to a result from the comparator, the data describing ratio between the reference voltage and the input voltage, and being used to set the required conversion gain ratio.

The gain controller may include a digital circuit; when the output voltage is below the threshold range below the reference voltage, the digital circuit may be configured to, through adjusting the conversion gain ratio, adjust the output voltage by a large amount.

The counter may be configured to count a predetermined number of clock periods every time after the switching frequency of the switch capacitor converter core is changed, so that there is sufficient time for the output voltage to respond to the change.

The clock generator may include a comparator; a logic circuit connected with the comparator and configured to drive the comparator; and a clock signal generator connected with the logic circuit and configured to output two clock signals. The two clock signals may be transmitted to the switch signal router and the switch driver, and further configured to control the switch capacitor converter core.

In another aspect, the present patent application provides a voltage converter for medical devices including: a switch capacitor converter core including a plurality of power transistor switches configured to receive an input voltage and output an output voltage; a switch driver connected with the switch capacitor converter core and configured to turn on corresponding power transistor switches in the switch capacitor converter core so as to supply power to a load receiving the output voltage; a switch signal router connected with the switch driver and configured to selectively transmit signals required by the switch driver; a gain selection decoder connected with the switch signal router; a gain controller connected with the gain selection decoder, the gain selection decoder being configured to decode gain selection instructions transmitted from the gain controller; an input adjusting device connected with the gain controller and configured to receive the input voltage and a reference voltage, to indicate relationship between the input voltage and the reference voltage, and to transmit the relationship to the gain controller; an output adjusting device connected with the gain controller and configured to receive the output voltage and the reference voltage, to indicate relationship between the output voltage and the reference voltage, and to transmit the relationship to the gain controller; a clock generator connected with the switch signal router, the gain controller and the output adjusting device; and a counter connected with the gain controller. The input adjusting device includes an adaptive ADC configured to determine a required conversion gain ratio based on the input voltage and the reference voltage, and a control logic circuit connected with the adaptive ADC and configured to control the adaptive ADC. The output adjusting device includes a plurality of comparators and a control logic circuit connected with the comparators. The gain controller is configured to control the conversion gain ratio required by the switch capacitor converter core according to information provided by the input adjusting device and the output adjusting device, the conversion gain ratio being the ratio between the output voltage and the input voltage. The gain controller includes a digital circuit. When the output voltage is out of a threshold range around the reference voltage, the digital circuit is configured to, through adjusting the conversion gain ratio, adjust the output voltage by a large amount. When the output voltage is in a threshold range around the reference voltage, the gain controller is turned off, and switching frequency of the switch capacitor converter core is adjusted by discrete amounts based on a DFS (Discrete-frequency Scaling) algorithm so that the output voltage gradually approaches the reference voltage.

The switch capacitor converter core may include a plurality of power transistor switches and a pump capacitor, and the conversion gain ratio provided by the switch capacitor converter core may be 1/2, 2/3, 1, 3/2 or 2.

The adaptive ADC in the input adjusting device may include a comparator and a plurality of latches, the latches being connected with the comparator and configured to generate data of a predetermined number of digits according to a result from the comparator, the data describing ratio between the reference voltage and the input voltage, and being used to set the required conversion gain ratio.

The clock generator may include a comparator; a logic circuit connected with the comparator and configured to drive the comparator; and a clock signal generator connected with the logic circuit and configured to output two clock signals. The two clock signals may be transmitted to the switch signal router and the switch driver, and further configured to control the switch capacitor converter core.

In yet another aspect, the present patent application provides a voltage converter for medical devices. The voltage converter includes: a switch capacitor converter core including a plurality of power transistor switches configured to receive an input voltage and output an output voltage; a switch driver connected with the switch capacitor converter core and configured to turn on corresponding power transistor switches in the switch capacitor converter core so as to supply power to a load receiving the output voltage; a switch signal router connected with the switch driver and configured to selectively transmit signals required by the switch driver; a gain selection decoder connected with the switch signal router; a gain controller connected with the gain selection decoder, the gain selection decoder being configured to decode gain selection instructions transmitted from the gain controller; an input adjusting device connected with the gain controller and configured to receive the input voltage and a reference voltage, to indicate relationship between the input voltage and the reference voltage, and to transmit the relationship to the gain controller; an output adjusting device connected with the gain controller and configured to receive the output voltage and the reference voltage, to indicate relationship between the output voltage and the reference voltage, and to transmit the relationship to the gain controller; a clock generator connected with the switch signal router, the gain controller and the output adjusting device; and a counter connected with the gain controller.

The input adjusting device may include an adaptive ADC configured to determine a required conversion gain ratio based on the input voltage and the reference voltage, and a control logic circuit connected with the adaptive ADC and configured to control the adaptive ADC.

The output adjusting device may include a plurality of comparators and a control logic circuit connected with the comparators.

The gain controller may be configured to control the conversion gain ratio required by the switch capacitor converter core according to information provided by the input adjusting device and the output adjusting device, the conversion gain ratio being the ratio between the output voltage and the input voltage.

When the output voltage is in a threshold range below the reference voltage, the gain controller may be turned off, and switching frequency of the switch capacitor converter core may be adjusted by discrete amounts based on a DFS (Discrete-frequency Scaling) algorithm so that the output voltage gradually approaches the reference voltage.

When the output voltage is equal to or greater than the reference voltage, the switch capacitor converter core may stop its switching operations.

When the output voltage is lower than the reference voltage, the switch capacitor converter core may be configured to resume its switching operations.

The switch capacitor converter core may include a plurality of power transistor switches and a pump capacitor, and the conversion gain ratio provided by the switch capacitor converter core may be 1/2, 2/3, 1, 3/2 or 2.

The adaptive ADC in the input adjusting device may include a comparator and a plurality of latches, the latches being connected with the comparator and configured to generate data of a predetermined number of digits according to a result from the comparator, the data describing ratio between the reference voltage and the input voltage, and being used to set the required conversion gain ratio.

The clock generator may include a comparator; a logic circuit connected with the comparator and configured to drive the comparator; and a clock signal generator connected with the logic circuit and configured to output two clock signals. The two clock signals may be transmitted to the switch signal router and the switch driver, and further configured to control the switch capacitor converter core.

BRIEF DESCRIPTION OF THE DRAWINGS

FIG. 2A is block diagram of an input adjusting device of the voltage converter depicted in FIG. 1.

FIG. 2B is block diagram of an output adjusting device of the voltage converter depicted in FIG. 1.

DETAILED DESCRIPTION

Reference will now be made in detail to a preferred embodiment of the voltage converter for medical devices disclosed in the present patent application, examples of which are also provided in the following description. Exemplary embodiments of the voltage converter for medical devices disclosed in the present patent application are described in detail, although it will be apparent to those skilled in the relevant art that some features that are not particularly important to an understanding of the voltage converter for medical devices may not be shown for the sake of clarity.

Furthermore, it should be understood that the voltage converter for medical devices disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
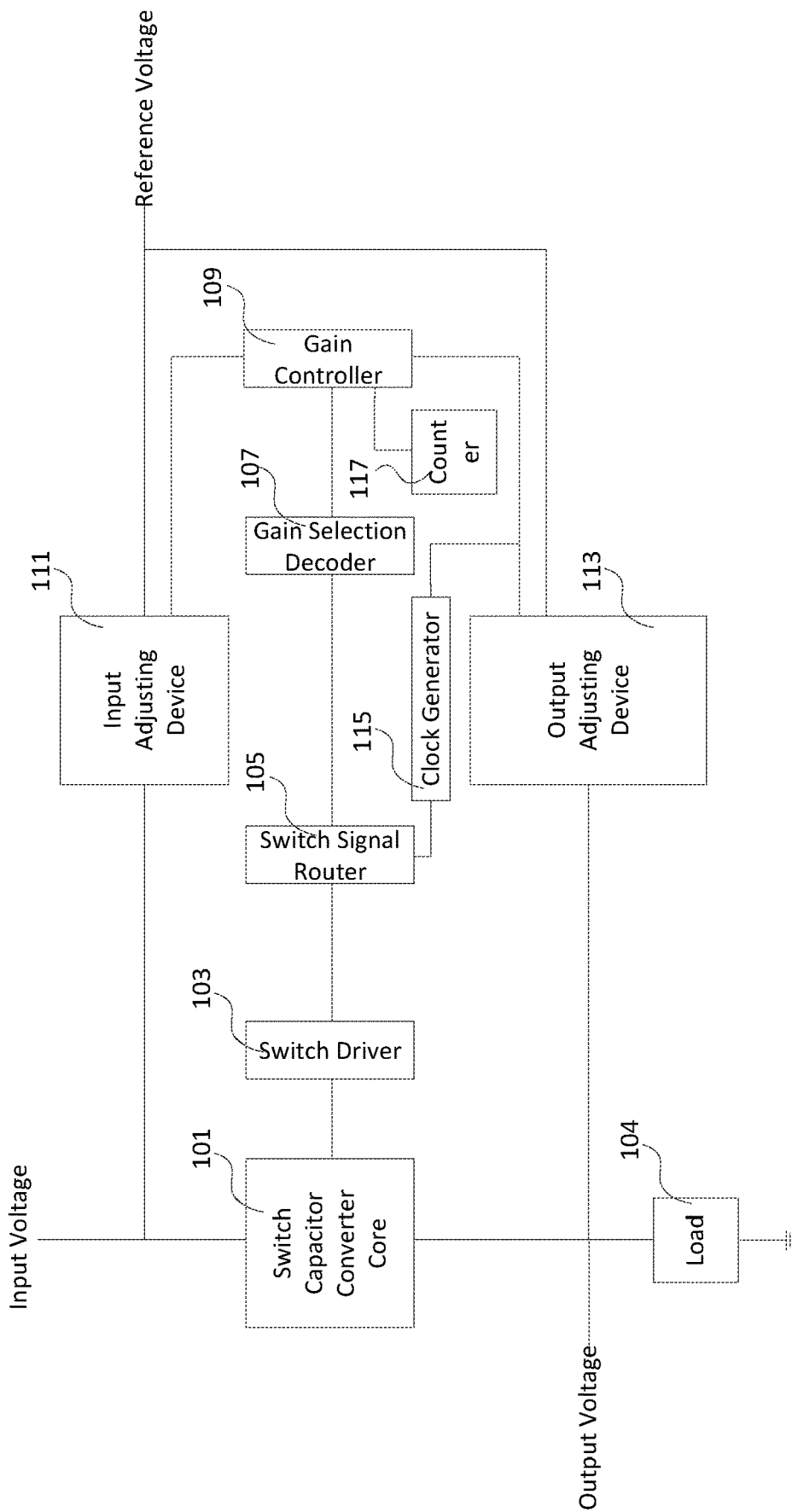
FIG. 1 is a block diagram of a voltage converter for medical devices in accordance with an embodiment of the present patent application.

FIG. 1 is a block diagram of a voltage converter for medical devices in accordance with an embodiment of the present patent application. Referring to FIG. 1, the voltage converter for medical devices includes a switch capacitor converter core 101 that includes a plurality of power transistor switches configured to receive an input voltage and output an output voltage; a switch driver 103 connected with the switch capacitor converter core 101 and configured to turn on corresponding power transistor switches in the switch capacitor converter core 101 so as to supply power to a load 104 receiving the output voltage; a switch signal router 105 connected with the switch driver 103 and configured to selectively transmit signals required by the switch driver 103; a gain selection decoder 107 connected with the switch signal router 105; a gain controller 109 connected with the gain selection decoder 107, the gain selection decoder 107 being configured to decode gain selection instructions transmitted from the gain controller 109; an input adjusting device 111 connected with the gain controller 109 and configured to receive the input voltage and a reference voltage, to indicate relationship between the input voltage and the reference voltage, and to transmit the relationship to the gain controller 109; an output adjusting device 113 connected with the gain controller 109 and configured to receive the output voltage and the reference voltage, to indicate relationship between the output voltage and the reference voltage, and to transmit the relationship to the gain controller 109; a clock generator 115 connected with the switch signal router 105, the gain controller 109 and the output adjusting device 113; and a counter 117 connected with the gain controller 109.

FIG. 2A is block diagram of an input adjusting device of the voltage converter depicted in FIG. 1. Referring to FIG. 2A, in this embodiment, the input adjusting device 111 includes an adaptive ADC 201 configured to determine a required conversion gain ratio based on the input voltage and the reference voltage, and a control logic circuit 203 connected with the adaptive ADC 201 and configured to control the adaptive ADC 201. Referring to FIG. 1 and FIG. 2A, in this embodiment, the adaptive ADC 201 in the input adjusting device 111 includes a comparator 204 and a plurality of latches 205. The latches 205 are connected with the comparator 204 and configured to generate data of a predetermined number of digits according to a result from the comparator 204. In this embodiment, the predetermined number of digits is 3. The 3-digit data describes ratio between the reference voltage and the input voltage, and is used to set the required conversion gain ratio. When the input voltage changes by a small amount, the 3-digit data generated by the latches 205 remains unchanged. When the input voltage changes by a relatively large amount, the 3 digit data generated by the latches 205 changes so as to change the conversion gain ratio.

FIG. 2B is block diagram of an output adjusting device of the voltage converter depicted in FIG. 1. Referring to FIG. 2B, in this embodiment, the output adjusting device 113 includes a plurality of comparators 211 and a control logic circuit 213 connected with the comparators 211. Each of the comparators 211 in the output adjusting device 113 includes a read amplifier. The use of the read amplifier helps with further lowering the system power consumption.

Referring to FIG. 1, the gain controller 109 is configured to control the conversion gain ratio required by the switch capacitor converter core 101 according to information provided by the input adjusting device 111 and the output adjusting device 113. The conversion gain ratio is the ratio between the output voltage and the input voltage.

In this embodiment, when the output voltage is sufficiently close to the reference voltage, for example, when the output voltage is in a threshold range below the reference voltage, the gain controller 109 is turned off, and the switching frequency of the switch capacitor converter core 101 is adjusted by discrete amounts based on a DFS (Discrete-frequency Scaling) algorithm so that the output voltage gradually approaches the reference voltage and fine-tuning of the output voltage is realized. When the output voltage reaches or exceeds the reference voltage, the switch capacitor converter core 101 stops its switching operations. When the output voltage is lower than the reference voltage, the switch capacitor converter core 101 is configured to resume its switching operations.

More specifically, referring to FIG. 1, the switch capacitor converter core 101 includes a plurality of power transistor switches and a pump capacitor. The conversion gain ratio may be greater or less than 1. In this embodiment, the conversion gain ratio provided by the switch capacitor converter core 101 may be 1/2, 2/3, 1, 3/2 or 2. The gain controller 109 includes a digital circuit. When the output voltage is out of a predetermined range (the reference voltage±a predetermined threshold), the digital circuit, through adjusting the conversion gain ratio, adjusts the output voltage by a relatively great amount, therefore realizing rough adjustment of the output voltage through adaptive power control.

When the output voltage is in the predetermined range (the reference voltage±a predetermined threshold), the gain controller 109 is turned off, the switching frequency of the switch capacitor converter core 101 is adjusted by discrete amounts based on a DFS (Discrete-frequency Scaling) algorithm so that the output voltage is fine tuned. The counter 117 is configured to count a predetermined number of clock periods every time after the switching frequency of the switch capacitor converter core 101 is changed, so that there is sufficient time for the output voltage to respond to the change. In this embodiment, the predetermined threshold is less than or equal to 10% of the reference voltage.

Figure 3:
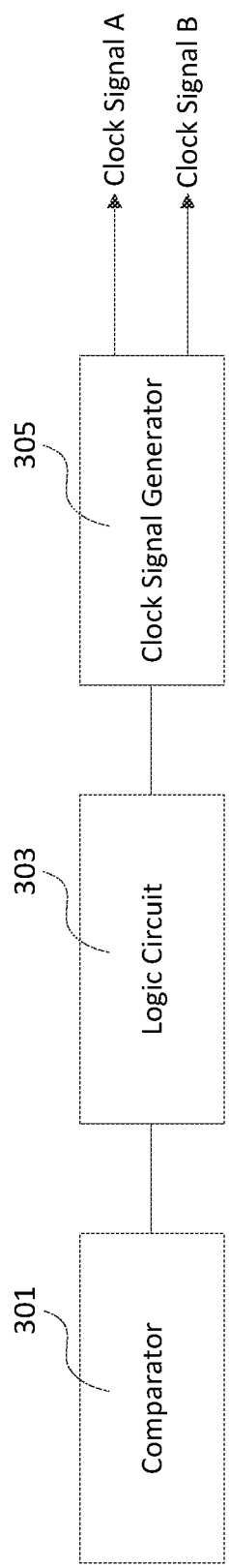
FIG. 3 is block diagram of a clock generator of the voltage converter depicted in FIG. 1.

FIG. 3 is block diagram of a clock generator of the voltage converter depicted in FIG. 1. Referring to FIG. 3, the clock generator 115 includes a comparator 301; a logic circuit 303 connected with the comparator 301 and configured to drive the comparator 301; and a clock signal generator 305 connected with the logic circuit 303 and configured to output two clock signals A and B. The two clock signals A and B are transmitted to the switch signal router 105 and the switch driver 103, and further configured to control the switch capacitor converter core 101. In this embodiment, the input of the comparator 301 is the output voltage and the reference voltage.

In another embodiment, when the output voltage is greater than the reference voltage, the switch driver 103 controls the power transistors in the switch capacitor converter core 101 to stop switching operations. This design further lowers power consumption of the system and limits the overshoot of the output voltage.

In the above embodiments, the voltage converter has a small chip area, circuits with low complexity, and high configurability, implementing the controlling method that combines the rough adjustment (adaptive power control) and the find adjustment (DFS) of the output voltage so that the voltage converter satisfies the requirements on the output voltage and the load in a wide range, and is especially suitable for supplying power to medical devices. In addition, when the output voltage is greater than the reference voltage, the switch driver is configured to control the power transistors of the switch capacitor converter core 101 to stop switching operations, which not only limits overshoot of the output voltage, but also further decreases power consumption of the system, so that the working efficiency of the system is improved.

While the present patent application has been shown and described with particular references to a number of embodiments thereof, it should be noted that various other changes or modifications may be made without departing from the scope of the present invention.

What is claimed is:

1. A voltage converter for medical devices, the voltage converter comprising:
    a switch capacitor converter core comprising a plurality of power transistor switches configured to receive an input voltage and output an output voltage;
    a switch driver connected with the switch capacitor converter core and configured to turn on corresponding power transistor switches in the switch capacitor converter core so as to supply power to a load receiving the output voltage;
    a switch signal router connected with the switch driver and configured to selectively transmit signals required by the switch driver;
    a gain selection decoder connected with the switch signal router;
    a gain controller connected with the gain selection decoder, the gain selection decoder being configured to decode gain selection instructions transmitted from the gain controller;
    an input adjusting device connected with the gain controller and configured to receive the input voltage and a reference voltage, to indicate relationship between the input voltage and the reference voltage, and to transmit the relationship to the gain controller; and
    an output adjusting device connected with the gain controller and configured to receive the output voltage and the reference voltage, to indicate relationship between the output voltage and the reference voltage, and to transmit the relationship to the gain controller; wherein:
    the gain controller comprises a digital circuit and is configured to control the conversion gain ratio required by the switch capacitor converter core according to information provided by the input adjusting device and the output adjusting device, the conversion gain ratio being the ratio between the output voltage and the input voltage.

2. The voltage converter for medical devices of claim 1, wherein when the output voltage is out of a threshold range around the reference voltage, the digital circuit is configured to, through adjusting the conversion gain ratio, adjust the output voltage by a large amount.

3. The voltage converter for medical devices of claim 2, wherein when the output voltage is in a threshold range around the reference voltage, the gain controller is turned off, and switching frequency of the switch capacitor converter core is adjusted by discrete amounts based on a DFS (Discrete-frequency Scaling) algorithm so that the output voltage gradually approaches the reference voltage.

4. The voltage converter for medical devices of claim 1 further comprising a clock generator connected with the switch signal router, the gain controller and the output adjusting device.

5. The voltage converter for medical devices of claim 4, wherein the clock generator comprises a comparator; a logic circuit connected with the comparator and configured to drive the comparator; and a clock signal generator connected with the logic circuit and configured to output two clock signals; the two clock signals are transmitted to the switch signal router and the switch driver, and further configured to control the switch capacitor converter core.

6. The voltage converter for medical devices of claim 1, wherein the input adjusting device comprises an adaptive ADC configured to determine a required conversion gain ratio based on the input voltage and the reference voltage, and a control logic circuit connected with the adaptive ADC and configured to control the adaptive ADC.

7. The voltage converter for medical devices of claim 1, wherein the output adjusting device comprises a plurality of comparators and a control logic circuit connected with the comparators.

8. The voltage converter for medical devices of claim 1, wherein the switch capacitor converter core comprises a plurality of power transistor switches and a pump capacitor, and the conversion gain ratio provided by the switch capacitor converter core is 1/2, 2/3, 1, 3/2 or 2.

9. The voltage converter for medical devices of claim 1, wherein the adaptive ADC in the input adjusting device comprises a comparator and a plurality of latches, the latches being connected with the comparator and configured to generate data of a predetermined number of digits according to a result from the comparator, the data describing ratio between the reference voltage and the input voltage, and being used to set the required conversion gain ratio.

* * * * *